(12) United States Patent
Hussein

(10) Patent No.: US 6,701,929 B2
(45) Date of Patent: Mar. 9, 2004

(54) DEVICE AND METHOD FOR TREATMENT OF CONGESTIVE HEART FAILURE

(76) Inventor: Hany Hussein, 8 Agostino, Newport Coast, CA (US) 92657

( * ) Notice: Subject to any disclaimer, the term of this patent is extended or adjusted under 35 U.S.C. 154(b) by 174 days.

(21) Appl. No.: 09/820,063

(22) Filed: Mar. 27, 2001

(65) Prior Publication Data

US 2001/0014811 A1 Aug. 16, 2001

Related U.S. Application Data

(60) Provisional application No. 60/122,714, filed on Mar. 3, 1999, and provisional application No. 60/192,174, filed on Mar. 27, 2000.

(51) Int. Cl.⁷ ................................................ A61B 19/00
(52) U.S. Cl. ...................................................... 128/898
(58) Field of Search ................................. 606/151, 157; 128/898

(56) References Cited

U.S. PATENT DOCUMENTS

| | | | | |
|---|---|---|---|---|
| 5,800,528 A | * | 9/1998 | Lederman et al. | 600/37 |
| 5,961,440 A | * | 10/1999 | Schweich et al. | 600/16 |
| 6,125,852 A | * | 10/2000 | Stevens et al. | 128/898 |

* cited by examiner

*Primary Examiner*—Gary Jackson
(74) *Attorney, Agent, or Firm*—James G. O'Neil; Klein Neill & Singh, LLP

(57) ABSTRACT

Devices for treatment of congestive heart failure include devices insertable over and clamped on all or a selected portion of the exterior of a heart. The devices may be introduced surgically, or under thoracoscopic control around a portion or all of the exterior of the heart.

6 Claims, 2 Drawing Sheets

DEVICE AND METHOD FOR TREATMENT OF CONGESTIVE HEART FAILURE

CROSS REFERENCE TO RELATED APPLICATION

This application is a continuation of abandoned provisional application, serial No. 60/122,714, filed Mar. 3, 1999, and claims the benefit of Provisional application Ser. No. 60/192,174, filed on Mar. 27, 2000.

BACKGROUND OF THE INVENTION

1. Field of the Invention

This invention relates generally to devices and methods of treating heart failure, and more particularly, to an improved device and method of treating congestive heart failure.

2. Description of Related Art

Heart failure caused by enlargement of the heart is a serious condition, which can cause death, if untreated. This condition is characterized by a reduction in cardiac index and ejection fraction. The well known "Batista" procedure aims to treat this condition surgically by removing a portion of the left ventricle wall, and suturing the remainder of this wall, thereby reducing the ventricular volume. This procedure also aims to approximate the mitral valve to prevent leakage of blood during contraction of the heart. However, the "Batista" procedure requires costly surgery, and results in significant mortality and morbidity. It would, therefore, be desirable to develop a treatment for heart failure utilizing a less invasive technique.

SUMMARY OF THE INVENTION

The present invention provides devices and methods for treatment of heart failure. The basic concept of the present invention involves a clamp, retainer, or staple (made from stainless steel, or the like).

Various configurations are proposed for the clamp, retainer, or staple. One embodiment consists of a clamp that permanently clamps and holds a portion of a ventricular wall in order to reduce ventricular volume while reducing wall tension within the ventricular wall. Further embodiments consist of devices or staples to contain and restrain all or a portion of the heart in order to reduce wall tension and enhance pumping action.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, wherein like reference numerals are used throughout the several views, and, in which:

DESCRIPTION OF PREFERRED EMBODIMENTS

The following description is provided to enable any person skilled in the art to make and use the invention, and sets forth the best modes contemplated by the inventor of carrying out his invention. Various modifications, however, will remain readily apparent to those skilled in the art, since the generic principles of the present invention have been defined herein specifically to provide for improved devices for constraining the heart and an improved method therefor.

Figure 1:
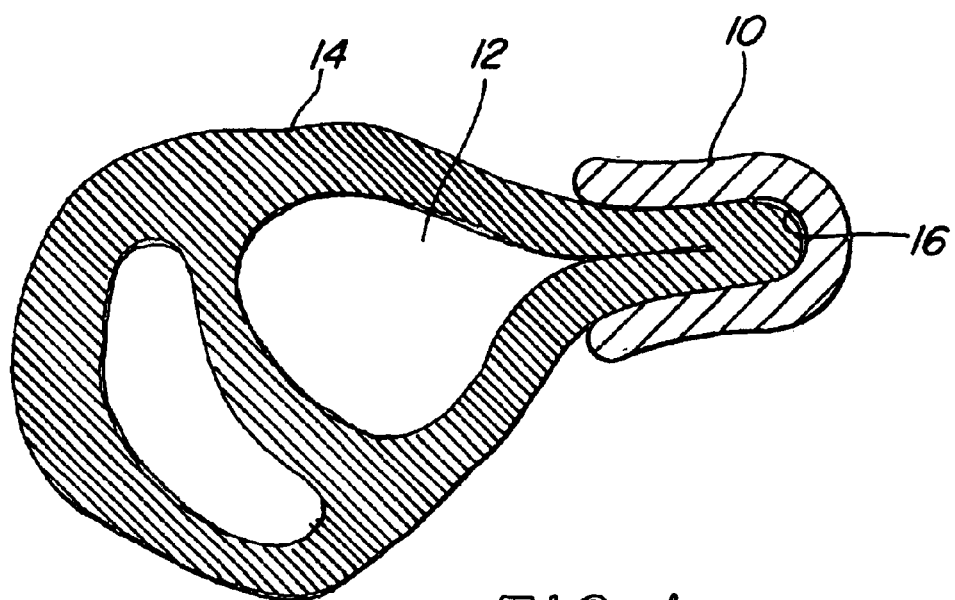
FIG. 1 is a cross-sectional view of a first embodiment of a clamp or retainer device for clamping and holding a portion of a heart wall in order to reduce the size of a ventricular cavity, and to reduce wall tension in a ventricular wall.

FIG. 1 shows a device 10 comprised of a clamp made from stainless steel, or the like. The device 10 is placed over and constrains a portion of a left ventricle 12 of a heart 14 so as to pinch or constrain the portion of the heart wall held between an open area 16 in the device 10. The device 10 may be of any desired length and include closed or open ends.

Figure 2:
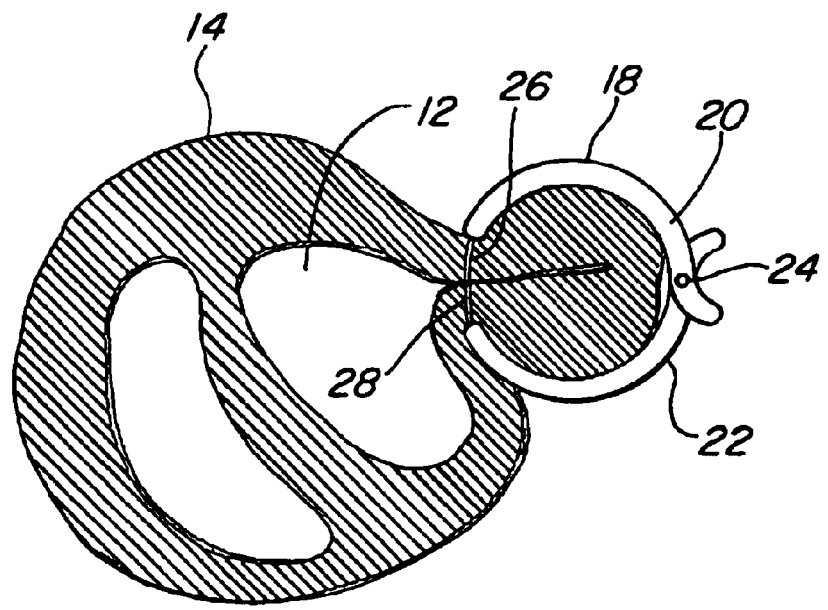
FIG. 2 is a cross-sectional view of a second embodiment comprising an alternate configuration of a device for clamping and holding a portion of a heart wall.

FIG. 2 shows a further device 18 comprised of a clamp having two movable pieces or segments 20, 22, secured together at a spring joint 24. Before this clamp 18 is placed over a portion of the left ventricle 12 of a heart 14, a portion of the inner wall of the left ventricle is secured or stapled together by securing elements or staples 26, 28. The securing elements 26, 28, together with the spring biased arms or pieces constrain the covered portion of the left ventricle. The device 18 is also of any desired length and may include closed or open ends.

Figure 3:
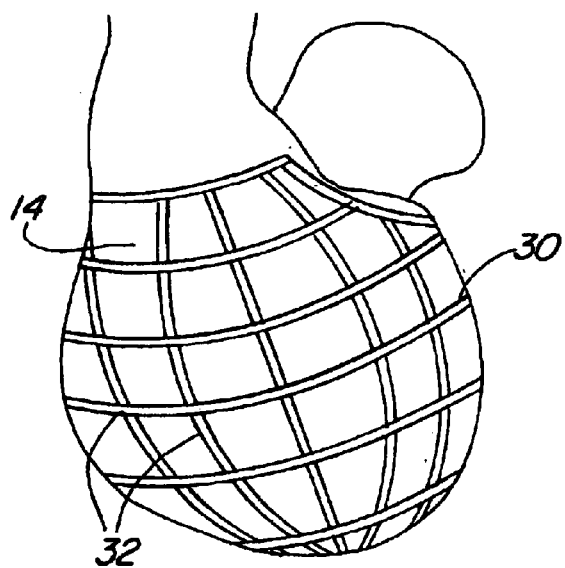
FIG. 3 is a front elevational view of a third embodiment comprising a device placed over and constraining an entire heart in order to enhance pumping action.

FIG. 3 illustrates a basket or mesh retainer 30 having a plurality of crossing strips 32 placed around and constraining substantially all of the entire outer wall of a heart 14.

Figure 4:
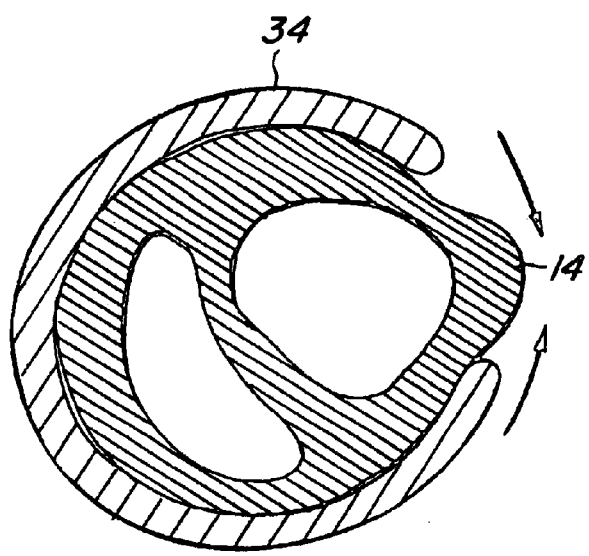
FIG. 4 is a cross-sectional view of a fourth embodiment comprising a further device that is placed over an entire heart for constraining the heart wall.

FIG. 4 illustrates a further retainer comprised of a shell 34, preferably made from a metal such as stainless steel, placed around and constraining the heart 14. The shell 34, substantially surrounds and constrains the exterior wall of heart 14.

Figure 5:
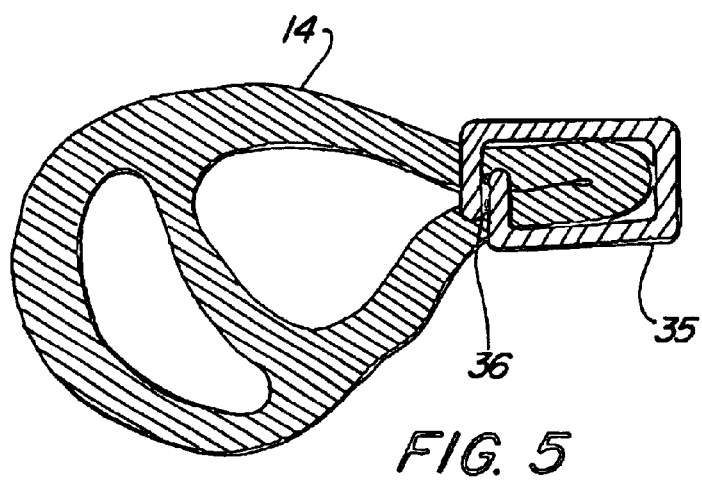
FIG. 5 is a cross-section of a heart showing one or more staples used to join and hold a portion of a ventricular wall.

FIG. 5 illustrates one or more large staples 35, preferably made from stainless steel, used to join and secure a portion of the ventricular wall of a heart 14. These large staples preferably including means for locking or securing 36 of the ends of the staples together.

Those skilled in the art will appreciate that various adaptations and modifications of the just-described preferred embodiments can be configured without departing from the scope and spirit of the invention. Therefore, it is to be understood that, within the scope of the appended claims, the invention may be practiced other than as specifically described herein.

What is claimed is:

1. A method for treatment of congestive heart failure, comprising:
   inserting a staple through a left ventricle of a heart to reduce the size or aid in pumping action of the heart and placing a clamp over the staple.

2. A device for treating congestive heart failure, comprising:
   a retainer adapted to be secured to at least a left ventricle of a heart and wherein the retainer is a staple adapted to secure walls of a left ventricle together; and a clamp is placed over the staple.

3. The device of claim 2 wherein the clamp is one piece.

4. The device of claim 2 wherein the clamp is made of two pieces hingedly secured together.

5. The device of claim 2 wherein the stable is a large staple adapted to be secured through a left ventricle of a heart to secure walls of the left ventricle together.

6. The device of claim 2, further including a securing elements at open ends of the staple to lock the open ends together.

* * * * *